(12) United States Patent
Qu et al.

(10) Patent No.: US 8,548,587 B2
(45) Date of Patent: Oct. 1, 2013

(54) DEVICES, SYSTEMS AND METHODS FOR CHARACTERIZING A TACHYCARDIA AND/OR SELECTING TREATMENT FOR A TACHYCARDIA USING RESULTS OF A FRACTIONATION ANALYSIS

(75) Inventors: Fujian Qu, Sunnyvale, CA (US); Timothy A. Fayram, Gilroy, CA (US); Michael E. Benser, Valencia, CA (US); Taraneh Ghaffari Farazi, San Jose, CA (US); Mark Carlson, Calabasas, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 274 days.

(21) Appl. No.: 13/090,079

(22) Filed: Apr. 19, 2011

(65) Prior Publication Data

US 2012/0271368 A1 Oct. 25, 2012

(51) Int. Cl.
*A61N 1/365* (2006.01)

(52) U.S. Cl.
USPC .................................. 607/14; 607/4; 600/518

(58) Field of Classification Search
None
See application file for complete search history.

(56) References Cited

U.S. PATENT DOCUMENTS

| | | | |
|---|---|---|---|
| 5,741,304 A * | 4/1998 | Patwardhan et al. | 607/5 |
| 7,072,715 B1 * | 7/2006 | Bradley | 607/17 |
| 7,076,300 B1 * | 7/2006 | Kroll et al. | 607/14 |
| 7,386,343 B1 | 6/2008 | Kroll | |
| 7,917,214 B1 * | 3/2011 | Gill et al. | 607/9 |
| 2005/0215914 A1 | 9/2005 | Bornzin | |
| 2005/0256545 A1 | 11/2005 | Koh | |
| 2007/0208260 A1 | 9/2007 | Afonso | |
| 2008/0200961 A1 | 8/2008 | Kroll | |
| 2010/0004550 A1 | 1/2010 | Ishay | |
| 2011/0208261 A1 * | 8/2011 | Levine et al. | 607/27 |
| 2012/0191154 A1 * | 7/2012 | Ryu et al. | 607/14 |

OTHER PUBLICATIONS

Gardener et al., "Electrophysiologic and Anatomic Basis for Fractionated Electrograms Recorded From Healed Myocardial Infarcts," Circulation, 1985, vol. 72, 596-611.
Nademanee et al., "A New Approach for Catheter Ablation of Atrial Fibrillation: Mapping of the Electrophysiologic Substrate," J. Am. Coll. Cardiol., 2004; 43:2044-2053.
Ng et al., "Technical Considerations for Dominant Frequency Analysis," J. Cardiovasc. Electrophysiol. Jul. 2007;18(7):757-764.
Ng at al., "Understanding and Interpreting Dominant Frequency Analysis of AF Electrograms," J. Cardiovasc. Electrophysiol. Jun. 2007;18(6):680-685.

* cited by examiner

*Primary Examiner* — Kennedy Schaetzle
(74) *Attorney, Agent, or Firm* — Theresa A. Raymer; Steven M. Mitchell

(57) ABSTRACT

Provided herein are implantable systems, and methods for use therewith, for characterizing a tachycardia and/or selecting treatment for a tachycardia using results of a fractionation analysis. One or more electrogram (EGM) signal(s) indicative of cardiac electrical activity are obtained. At least one of the EGM signal(s) is analyzed to determine whether the EGM signal is fractionated, and the results of the analyzing are used to characterize a tachycardia and/or to select treatment for a tachycardia.

13 Claims, 5 Drawing Sheets

DEVICES, SYSTEMS AND METHODS FOR CHARACTERIZING A TACHYCARDIA AND/OR SELECTING TREATMENT FOR A TACHYCARDIA USING RESULTS OF A FRACTIONATION ANALYSIS

CROSS-REFERENCE TO RELATED APPLICATION

The present application relates to commonly invented and commonly assigned U.S. patent application Ser. No. 13/018,036, entitled DEVICES, SYSTEMS AND METHODS FOR CHARACTERIZING A TACHYCARDIA AND/OR SELECTING TREATMENT FOR A TACHYCARDIA USING RESULTS OF A DOMINANT FREQUENCY ANALYSIS, now abandoned, filed the same day as the present application.

FIELD OF THE INVENTION

Embodiments of the present invention relate to devices, systems and methods for characterizing a tachycardia and/or selecting treatment for a tachycardia.

BACKGROUND OF THE INVENTION

An arrhythmia is an abnormal heart rhythm where a patient's heartbeats may be irregular, too slow (bradycardia), or too rapid (tachycardia), and may originate in the atria or ventricles. Atrial tachycardia (AT) and ventricular tachycardia (VT) (collectively referred to as tachycardia) are forms of arrhythmia in which the atria or ventricles contract at a high rate; e.g., 100 or more beats per minute. A tachycardia can be life-threatening because it can lead to fibrillation, in which the heart beats rapidly in a chaotic, purposeless fashion such that the heart cannot pump blood effectively to the body. If untreated, fibrillation can be fatal.

Treatment for tachycardias can include anti-tachycardia pacing (ATP), which attempts to restore a more normal heart rhythm, and is often delivered via an implantable medical device. However, existing ATP techniques may not always be effective since these techniques of delivering ATP are typically unguided and deployed on a trial and error basis. Often, ATP is discontinued after multiple attempts and the implantable medical device is programmed to deliver a defibrillation shock to the heart in an attempt to terminate the tachycardia. However, shock therapy can be painful and can cause damage to the myocardium.

Accordingly, it would be beneficial to provide improved techniques for characterizing a tachycardia and/or selecting treatment for a tachycardia.

SUMMARY

Certain embodiments of the present invention relate to implantable systems and methods for use therewith, for characterizing a tachycardia and/or selecting treatment for a tachycardia using results of a dominant frequency analysis. In an embodiment, one or more electrodes implanted within, on and/or around a patient's heart are used to obtain one or more electrogram (EGM) signal(s) indicative of cardiac electrical activity. For at least one of the EGM signal(s) a dominant frequency (DF) analysis is performed, and the results of the DF analysis are used to characterize a tachycardia and/or to select treatment for a tachycardia. In certain embodiments, an analysis other than a DF analysis is used to detect a tachycardia.

In certain embodiments, results of a DF analysis are used to determine whether to deliver anti-tachycardia pacing (ATP) to attempt to terminate a tachycardia, or whether to deliver a shock to attempt to terminate the tachycardia without first delivering ATP. For example, in accordance with an embodiment, where results of a DF analysis include a detected DF, a determination of whether to deliver ATP to attempt to terminate a tachycardia, or whether to deliver a shock to attempt to terminate the tachycardia without first delivering ATP, is based on a comparison of the detected DF to a threshold. If the detected DF is below the threshold, ATP is delivered to attempt to terminate the tachycardia. Alternatively, if the detected DF is above the threshold, a shock is delivered to attempt to terminate the tachycardia without first delivering ATP.

In accordance with an embodiment, where results of a DF analysis include a detected DF variation, a determination of whether to deliver ATP to attempt to terminate a tachycardia, or whether to deliver a shock to attempt to terminate the tachycardia without first delivering ATP, is based on a comparison of the detected DF variation to a DF variation threshold. If the detected DF variation is below the DF variation threshold, then ATP is delivered to attempt to terminate the tachycardia. Alternatively, if the detected DF threshold is above the threshold, then a shock is delivered to attempt to terminate the tachycardia without first delivering ATP.

In accordance with an embodiment, where results of a DF analysis include a detected DF mean and a detected DF variation, a determination of whether to deliver ATP to attempt to terminate a tachycardia, or whether to deliver a shock to attempt to terminate the tachycardia without first delivering ATP, is based on a comparison of the detected DF mean to a DF mean threshold, and a comparison of the detected DF variation to a DF variation threshold.

Additionally, in accordance with an embodiment, results of a DF analysis are used to determine a rate at which to deliver ATP to attempt to terminate a tachycardia.

In accordance with an embodiment, a plurality of EGM signals is obtained, where each of the EGM signals is obtained using a different sensing vector and thereby is indicative of cardiac electrical activity associated with a different cardiac region. For at least two of the EGM signals a DF analysis is performed, and the results of the DF analysis of at least two of the EGM signals are used to characterize a tachycardia and/or to select a treatment for a tachycardia.

In accordance with an embodiment, results of a DF analysis for at least two EGM signals is used to determine whether to deliver ATP to attempt to terminate a tachycardia, or whether to deliver a shock to attempt to terminate the tachycardia without first delivering ATP. Additionally, in certain embodiments, results of a DF analysis for at least two EGM signals are used to select a pacing vector to use for delivering ATP.

Certain embodiments of the present invention relate to implantable systems and methods for use therewith, for characterizing a tachycardia and/or selecting treatment for a tachycardia based upon a determination of whether an EGM signal is fractionated. In an embodiment, one or more electrodes implanted within, on and/or around a patient's heart are used to obtain one or more electrogram (EGM) signal(s) indicative of cardiac electrical activity. At least one of the EGM signal(s) is analyzed to determine whether the EGM signal is fractionated, and the results of the analysis are used to characterize a tachycardia and/or to select treatment for a tachycardia. In certain embodiments, an analysis other than a fractionation analysis is used to detect a tachycardia.

In accordance with an embodiment, results of analyzing the at least one of the EGM signal(s) to determine whether the EGM signal is fractionated are used to determine whether to deliver anti-tachycardia pacing (ATP) to attempt to terminate a tachycardia, or whether to deliver a shock to attempt to terminate the tachycardia without first delivering ATP. For example, in accordance with an embodiment, where only one EGM signal is analyzed to determine whether the one EGM signal is fractionated, and the one EGM signal analyzed is determined to not be fractionated, then ATP is delivered to attempt to terminate the tachycardia. Alternatively, where only one EGM signal is analyzed to determine whether the one EGM signal is fractionated, and the one EGM signal is determined to be fractionated, then a shock is delivered to attempt to terminate the tachycardia, without first delivering ATP.

Additionally, in accordance with an embodiment, where results of analyzing the one EGM signal include determining that the one EGM signal is fractionated, a complexity metric indicative of a complexity of the fractionated EGM signal is determined. This complexity metric can be used to select a treatment for a tachycardia. For example, where the one EGM signal is determined to be fractionated and the complexity metric does not exceed a complexity threshold, then ATP is delivered to attempt to terminate the tachycardia. Alternatively, where the one EGM signal is determined to be fractionated and the complexity metric exceeds the complexity threshold, a shock is delivered to attempt to terminate the tachycardia, without first delivering ATP. Where results of analyzing the one EGM signal include determining that the one EGM signal is not fractionated, then ATP is delivered to attempt to terminate the tachycardia.

In accordance with an embodiment, the complexity metric indicative of a complexity of the fractionated EGM signal can be based on a deflection metric indicative of a number of deflections in the fractionated EGM signal, an amplitude metric indicative of an amplitude of one or more deflections in the fractionated EGM signal, and/or an interval metric indicative of an interval of time between two or more deflections in the fractionated EGM signal.

In accordance with an embodiment, a plurality of EGM signals are analyzed to determine whether each of the analyzed EGM signals is fractionated, and the results of analyzing the plurality of EGM signals are used to characterize a tachycardia and/or to select a treatment for a tachycardia. For example, in accordance with an embodiment, results of analyzing the plurality of EGM signals are used to determine whether to deliver ATP to attempt to terminate a tachycardia, or whether to deliver a shock to attempt to terminate the tachycardia without first delivering ATP. Additionally, in certain embodiments, results of the analysis are used to select a pacing vector to use for delivering ATP.

In accordance with an embodiment, where results of analyzing the plurality of EGM signals includes determining that at least one of the plurality of EGM signals analyzed is not fractionated, then ATP is delivered to attempt to terminate the tachycardia. Alternatively, where results of analyzing the plurality of EGM signals include determining that all of the EGM signals analyzed are fractionated, then a shock is delivered to attempt to terminate the tachycardia, without first delivering ATP.

In certain embodiments, for each EGM signal determined to be fractionated, a complexity metric indicative of a complexity of the fractioned EGM signal is determined, and a pacing vector is selected to use for delivering ATP based on the complexity metric determined for each EGM signal determined to be fractionated.

Additional and alternative embodiments, features and advantages of the invention will appear in the following description in which the preferred embodiments have been set forth in detail, in conjunction with the accompanying drawings and claims.

DETAILED DESCRIPTION OF THE INVENTION

Figure 1:
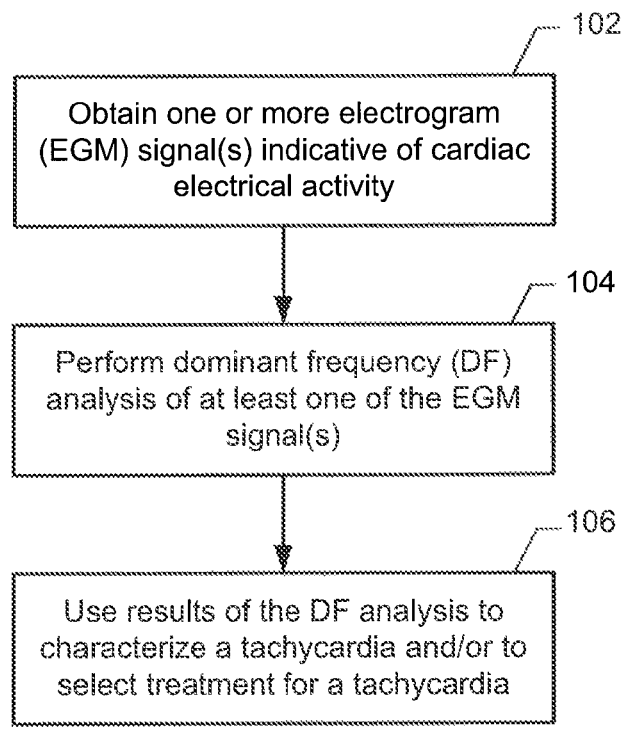
FIG. 1 is a high level flow diagram that is used to explain various embodiments of the present invention that can be used to characterize a tachycardia and/or to select treatment for a tachycardia using results of a dominant frequency analysis.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

Dominant Frequency Analysis

The high level flow diagram of FIG. 1 will now be used to explain various embodiments of the present invention that can be used to characterize a tachycardia and/or to select treatment for a tachycardia using results of a dominant frequency analysis. Such embodiments can be implemented by an implantable system, examples of which are discussed below with reference to FIGS. 4 and 5. In FIG. 1 and the other flow diagrams described herein, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the implantable system. Those skilled in the art may readily write such a control program based on the flow diagram and other descriptions presented herein.

Referring to FIG. 1, at step 102, one or more electrogram (EGM) signal(s) indicative of cardiac electrical activity is/are obtained. The EGM signal(s) is obtained using, e.g., one or more electrodes implanted within, on and/or around a patient's heart. Examples of electrodes and circuitry that can be used to obtain the EGM signal(s) are discussed below with reference to FIGS. 4 and 5. To simplify the embodiments described in FIGS. 1, 2A-2C and 3, reference will often be made to a single obtained EGM signal. However, embodiments using more than one obtained EGM signal are within the scope of the present invention, and will also be explained below.

At step 104, a dominant frequency (DF) analysis is performed on at least one of the EGM signal(s) obtained at step 102. In accordance with an embodiment, DF analysis of an EGM signal can include analyzing the EGM signal in the frequency domain to determine the strength of various frequency components of the EGM signal. The frequency component having the highest strength is the DF of the EGM signal. In accordance with an embodiment, a Fourier transform is used to analyze an EGM signal in the frequency domain to determine the signal's DF. Additionally, or alternatively, other techniques are used to analyze an EGM signal in the frequency domain, such as, but not limited to, discrete Fourier transform and/or Fast Fourier transform. In accordance with an embodiment, detecting a DF of an EGM signal can include separately filtering of the EGM signal using a plurality of different bandpass or notch filters in parallel, each of which has a different pass band or notch, and detecting the DF based on which filter's output includes the signal with the greatest amplitude. Variation of the DF, as well as mean of the DF (also referred to as DF variation and DF mean respectively), can also be determined as part of the DF analysis, as will be described below with reference to FIG. 2B and FIG. 2C.

At step 106, the results of the DF analysis (e.g., the detected DF, and/or DF variation and/or DF mean) are used to characterize the tachycardia and/or to select treatment for the tachycardia. For example, a DF, and/or DF variation and/or DF mean is used to characterize a tachycardia as stable or unstable. In accordance with an embodiment, selecting treatment can be determining between delivering ATP to attempt to terminate the tachycardia, or delivering a shock to attempt to terminate the tachycardia without first delivering ATP. In accordance with an embodiment, where a tachycardia is determined to be relatively stable, the tachycardia may be amendable to ATP to attempt to terminate the tachycardia, while a relatively unstable tachycardia may require a shock to attempt to terminate the tachycardia without first delivering ATP.

Figure 2A:
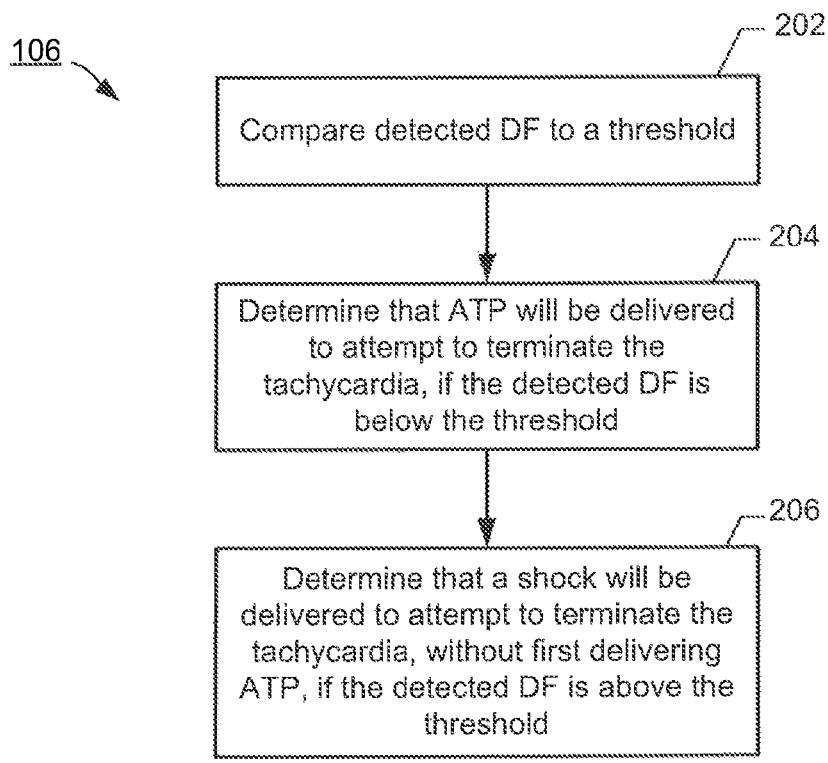
FIG. 2A is a high level flow diagram that is used to explain embodiments of the present invention that can be used for selecting therapy when a dominant frequency is detected as part of the dominant frequency analysis.

FIG. 2A will now be used to describe additional details of step 106 where a result of a DF analysis is a detected DF. At step 202, the detected DF is compared to a DF threshold. In accordance with an embodiment, the DF threshold is used for selecting a therapy to attempt to terminate a tachycardia. For example, since it is believed that the lower the DF the more likely that ATP can be used to successfully terminate a tachycardia, and that the higher the DF the more likely a shock will be needed to terminate a tachycardia, the DF threshold can be set such that a DF below a DF threshold triggers ATP to attempt to terminate the tachycardia while a DF above the DF threshold triggers a shock to attempt to terminate the tachycardia without first delivering ATP.

At step 204, if the detected DF is below the DF threshold, then ATP will be delivered to attempt to terminate the tachycardia. Alternatively, at step 206, if the detected DF is above the DF threshold, then a shock will be delivered to attempt to terminate the tachycardia without first delivering ATP. In accordance with an embodiment, in those cases where ATP is delivered but does not terminate the tachycardia within a predetermined amount of time, a shock can thereafter be delivered to attempt to terminate the tachycardia.

The results of step 202 can also be used to characterize a tachycardia. For example, the detected DF itself can characterize the tachycardia. For another example, if the DF is below the DF threshold then the tachycardia can be characterized as relatively stable, and if the DF is above the DF threshold then the tachycardia can be considered relatively unstable. Additionally DF thresholds can be used where there is a desire to more particularly characterize a tachycardia. For example, if four thresholds are used, then a tachycardia can be characterized as being very stable, relatively stable, relatively unstable, or very unstable. These are just a few examples, which are not meant to be limiting.

Figure 2B:
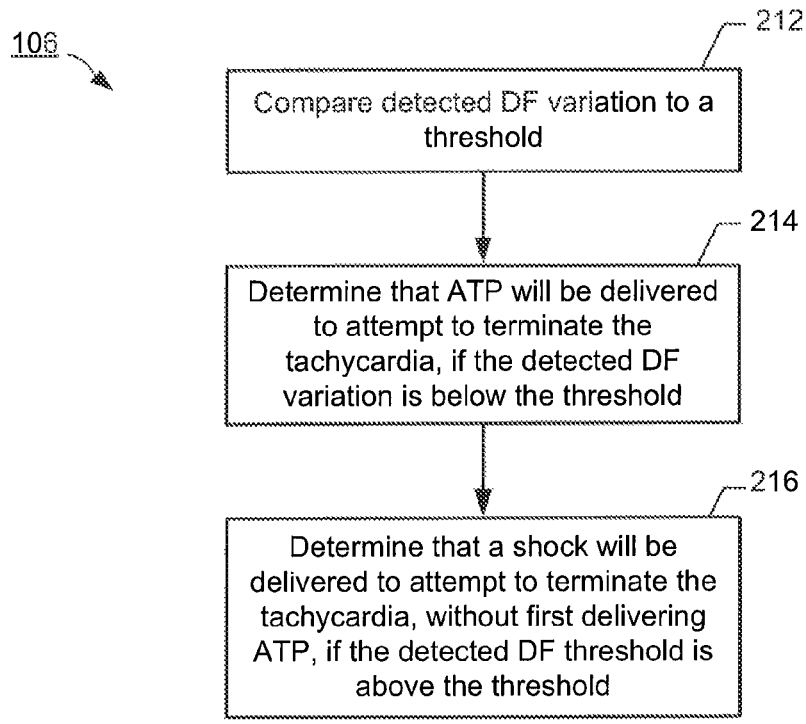
FIG. 2B is a high level flow diagram that is used to explain embodiments of the present invention that can be used for selecting therapy when a dominant frequency variation is detected as part of the dominant frequency analysis.

FIG. 2B will now be used to describe additional details of step 106 where a result of a DF analysis is a detected DF variation. In accordance with an embodiment, a DF variation can be detected by determining a DF for a plurality of windows of an EGM signal, where each window corresponds to X seconds worth of the EGM signal (e.g., X=4). The DF variation can be determined by calculating the standard deviation, interquartile range, range, mean difference, median absolute deviation, average absolute deviation (or simply average deviation), coefficient of variation, quartile coefficient of dispersion, relative mean difference, variance (the square of the standard deviation) or variance-to-mean ratio, of the DF for the plurality of windows of the EGM signal.

At step 212, the detected DF variation is compared to a DF variation threshold. In accordance with an embodiment, a DF variation threshold is used for selecting a therapy to attempt to terminate a tachycardia. For example, since it is believed that the lower the DF variation the more likely that ATP pacing can be used to successfully terminate a tachycardia, and that the higher the DF variation the more likely a shock will be needed to terminate a tachycardia, the DF variation threshold can be set such that a DF variation below the DF variation threshold triggers ATP therapy while a DF variation above the DF variation threshold triggers a shock to attempt to terminate the tachycardia without first delivering ATP.

At step 214, ATP is delivered to attempt to terminate the tachycardia, if the detected DF variation is below the DF variation threshold. Alternatively, at step 216, a shock is delivered to attempt to terminate the tachycardia without first delivering ATP if the detected DF is above the DF variation threshold.

The results of step 212 can also be used to characterize a tachycardia. For example, the detected DF variation itself can characterize the tachycardia. For another example, if the detected DF variation is below the DF variation threshold then the tachycardia is characterized as relatively stable, and if the DF variation is above the DF variation threshold then the tachycardia is considered relatively unstable. Additionally DF variation thresholds can be used where there is a desire to more particularly characterize a tachycardia.

Figure 2C:
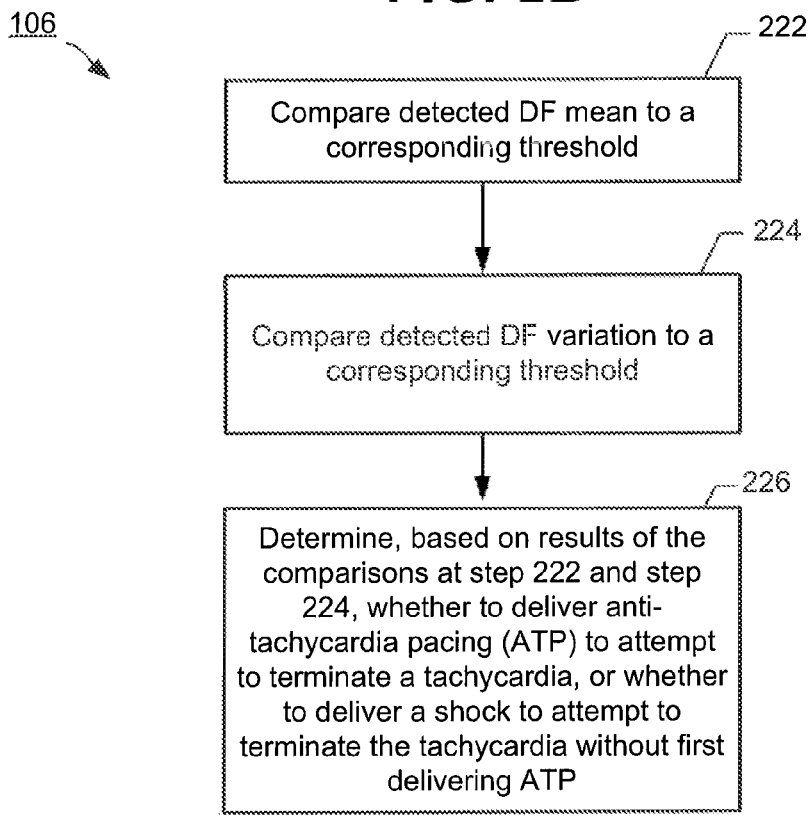
FIG. 2C is a high level flow diagram that is used to explain embodiments of the present invention that can be used for selecting therapy when a dominant frequency mean and a dominant frequency variation is detected as part of the dominant frequency analysis.

FIG. 2C will now be used to describe additional details of step 106 where a result of the DF analysis is a detected DF mean and a detected DF variation. In accordance with an embodiment, the detected DF mean can be the mean (i.e., average) DF detected for a plurality of windows of time. Details of how to detect a DF variation were explained above with reference to FIG. 2B, and thus, need not be repeated.

At step 222, the detected DF mean is compared to a DF mean threshold, and at step 224 the detected DF variation is compared to a DF variation threshold. Based on results of steps 222 and 224, there is a determination of whether to deliver ATP to attempt to terminate a tachycardia, or whether to deliver a shock to attempt to terminate the tachycardia without first delivering ATP, as indicated at step 226. For example, if the detected DF mean is below the DF mean threshold, and the DF variation is below the DF variation threshold, then ATP is delivered to attempt to terminate the tachycardia. Alternatively, if the detected DF mean is above the DF mean threshold, and the DF variation is above the DF variation threshold, then a shock is delivered to attempt to terminate the tachycardia without first delivering ATP. In one embodiment, if only one of the DF mean threshold and DF variation threshold is exceeded, then ATP is delivered to attempt to terminate the tachycardia. In an alternative embodiment, if at least one of the DF mean threshold and DF variation threshold is exceeded, then a shock is delivered to attempt to terminate the tachycardia without first delivering ATP. Other variations are also possible, and within the scope of the present invention.

The results of step 222 and 224 can also be used to characterize a tachycardia. For example, the detected DF mean and DF variation themselves can characterize the tachycardia. For another example, if the detected DF mean is below the DF mean threshold, and the DF variation is below the DF variation threshold, then the tachycardia is characterized as stable. If only one of the DF mean threshold and DF variation threshold is exceeded, then the tachycardia is considered relatively unstable. If both of the DF mean threshold and DF variation threshold is exceeded, then the tachycardia is considered very unstable. Other variations are also possible, and within the scope of the present invention.

In accordance with an embodiment, the thresholds referred to in FIGS. 2A-2C (e.g., the DF threshold in FIG. 2A, the DF variation threshold in FIG. 2B, and the DF mean and DF variation thresholds in FIG. 2C) can be defined based on a database of compiled DFs, DF variations and/or DF means obtained from a broad patient population, along with information specifying a treatment (e.g., ATP or shock) that was successful or unsuccessful in terminating a tachycardia. For example, where ATP has generally been successful in terminating tachycardias characterized by a first range of DFs but has generally been unsuccessful in terminating tachycardias characterized by a second range of DFs, a DF threshold can be set such that a detected DF less than the DF threshold triggers the delivery of ATP to attempt to terminate the tachycardia, while a detected DF above the DF threshold triggers a shock to attempt to terminate the tachycardia without first delivering ATP. In accordance with an embodiment, a DF variation threshold and a DF mean threshold can be defined in a similar manner as the DF threshold. It is also within the scope of the present invention that such threshold(s) can be tailored to a specific patient, i.e., not just set based on a broad patient population.

Embodiments of FIGS. 1, 2A-2C and 3 have been generally described as being implemented using a single EGM signal. However, embodiments described herein are also useful where a plurality of EGM signals are obtained and included in a DF analysis. For example, accordance with an embodiment, a plurality of EGM signals (e.g., at least two EGM signals) are obtained at step 102, where each of the EGM signals is obtained using a different sensing vector and thereby is indicative of cardiac electrical activity associated with a different cardiac region. In accordance with an embodiment, a DF analysis is performed on at least two of the EGM signals at step 104, and results of the DF analysis are used to characterize a tachycardia and/or to select a treatment for a tachycardia at step 106. In accordance with a specific embodiment, results of the DF analysis of at least two of the EGM signals can be used to characterize a tachycardia as stable or unstable, and/or used to select between delivering ATP to attempt to terminate the tachycardia and delivering a shock to attempt to terminate the tachycardia without first delivering ATP.

Embodiments will now be described where results of a DF analysis of at least two EGM signals are used to determine whether to deliver ATP to attempt to terminate a tachycardia, or whether to deliver a shock to attempt to terminate the tachycardia without first delivering ATP. In accordance with an embodiment, DFs are detected for at least two EGM signals. The detected DFs for the EGM signals are each compared to a DF threshold to determine whether to deliver ATP to attempt to terminate a tachycardia, or whether to deliver a shock to attempt to terminate the tachycardia without first delivering ATP. If the detected DF for each EGM signal is below the DF threshold, then ATP can be delivered to attempt to terminate the tachycardia. Alternatively, if the detected DF for each EGM signal is above the DF threshold, then a shock is delivered to attempt to terminate the tachycardia without first delivering ATP.

In certain embodiments, where one of the at least two detected DFs is below the DF threshold, then ATP is delivered to attempt to terminate the tachycardia. Alternatively, where one of the at least two detected DFs is above the DF threshold, then a shock is delivered to attempt to terminate the tachycardia without first delivering ATP. Other variations are also within the scope of the present invention.

Additionally, or alternatively, detected DFs for at least two of the EGM signals are compared to one another to determine whether to deliver ATP to attempt to terminate a tachycardia, or whether to deliver a shock to attempt to terminate the tachycardia without first delivering ATP. For example, in accordance with an embodiment, the closer the DFs of the EGM signals are to one another, presumably the less complex the tachycardia, and thus the more likely that the tachycardia could be terminated using ATP. Alternatively, the more the DFs of the EGM signals differ from one another, presumably the more complex the tachycardia, and thus the more likely that a shock may be needed to terminate the tachycardia. Accordingly, if the difference in DFs is less than a difference threshold, then ATP is delivered to attempt to terminate the tachycardia. Alternatively, if the difference in DFs is above the difference threshold, then a shock is delivered to attempt to terminate the tachycardia without first delivering ATP.

In accordance with another embodiment, DF variations are detected for at least two EGM signals. The detected DF variations for the EGM signals are compared to a DF variation threshold to determine whether to deliver ATP to attempt to terminate a tachycardia, or whether to deliver a shock to attempt to terminate the tachycardia without first delivering ATP. If the detected DF variation for each EGM signal is below the DF variation threshold, then ATP is delivered to attempt to terminate the tachycardia. Alternatively, where the detected DF variation for each EGM signal is above the DF variation threshold, then a shock is delivered to attempt to terminate the tachycardia without first delivering ATP.

In certain embodiments, where one of the at least two detected DF variations is below the DF variation threshold, then ATP is delivered to attempt to terminate the tachycardia. Alternatively, where one of the at least two detected DF variations is above the DF threshold, then a shock is delivered to attempt to terminate the tachycardia without first delivering ATP. Other variations are also within the scope of the present invention.

Embodiments will now be described where the determination is to deliver ATP to attempt to terminate a tachycardia, and the results of a DF analysis for at least two EGM signals are used to select a pacing vector to use for delivering ATP. In accordance with an embodiment, results of the DF analysis of at least two EGM signals include at least two detected DFs (i.e., a DF for each EGM signal), and the detected DFs for the EGM signals are compared to one another in order to determine where ATP is to be delivered.

In one embodiment, ATP is delivered using a pacing vector that is closest to the sensing vector used to obtain the EGM signal having the lowest DF, since the cardiac tissue paced by such a pacing vector is believed to be the most likely to be capable of being captured during an excitable gap, thereby enabling the pacing to eliminate excitable substrates and terminate the tachycardia. Depending on implementation, a pacing vector that is closest to a sensing vector may or may not comprise the exact same electrodes as the sensing vector.

In an alternative embodiment, ATP is delivered using a pacing vector that is closest to the sensing vector used to obtain the EGM signal having the highest DF, since the cardiac tissue paced by such a pacing vector is believed to be potentially closest to the source (i.e., the driver) of the tachycardia, and thereby may be susceptible to being overdriven by the pacing, and thus enabling the pacing to take control of and terminate the tachycardia.

In accordance with another embodiment, results of a DF analysis of at least two EGM signals include at least two detected DF variations, and the detected DF variations are compared to one another. ATP can delivered using a pacing vector that is closest to the sensing vector used to obtain the EGM signal having the lowest DF variation, since the cardiac tissue paced by such a pacing vector is believed to be the most likely to be captured during an excitable gap, thereby enabling the pacing to eliminate excitable substrates and terminate the tachycardia.

In an alternative embodiment, ATP is delivered using a pacing vector that is closest to the sensing vector used to obtain the EGM signal having the highest DF variation, since the cardiac tissue paced by such a pacing vector is believed to be potentially closest to the source (i.e., the driver) of the tachycardia and thereby may susceptible to being overdriven by the pacing thereby enabling the pacing to take control of and terminate the tachycardia.

In certain embodiments, in those cases where ATP is delivered but does not terminate the tachycardia within a predetermined amount of time, a shock can thereafter be delivered to attempt to terminate the tachycardia. Additionally, or alternatively, the results of a DF analysis are used to determine a rate at which to deliver ATP to attempt to terminate a tachycardia. In accordance with an embodiment, where only a single EGM signal is being analyzed as part of the DF analysis, the rate of ATP is equal to k*DF, where k is greater or equal to one (e.g., k=1.2). Where DF analysis is performed on multiple EGM signals, then ATP is equal to k times the highest DF detected. In accordance with an embodiment, ATP is delivered using a single pacing vector, or using multiple pacing vectors. Where multiple pacing vectors are used, which is often referred to as multi-site pacing, the ATP rate is set differently for different pacing vectors, e.g., ATP delivered using each pacing vector is delivered using a rate equal to k times the DF associated with a corresponding sensing vector (or different constants can be used for the different pacing vectors).

A DF analysis may be computationally (and thus, power and time) intensive. Thus, in certain embodiments the DF analysis is only performed after a tachycardia is detected using a less computationally intensive technique, such as, but not limited to, a technique that detects a tachycardia by comparing detected R-R intervals or heart rate to a corresponding threshold, which is well known in the art. In accordance with certain embodiments, if a tachycardia is detected that includes R-R intervals below a corresponding ventricular fibrillation (VF) interval threshold (or a heart rate above a corresponding VF rate threshold), then DF analysis can be skipped and a shock can be immediately delivered to attempt to terminate the VF as quickly as possible. In other embodiments, VF can initially be treated using ATP if the results of the DF analysis indicate that there is a good likelihood that ATP can be used to terminate the VF.

In accordance with other embodiments, results of the DF analysis are used to detect a tachycardia. For example, in accordance with an embodiment, where results of the DF analysis include a detected DF, a determination of whether a tachycardia is detected is based on a comparison of the detected DF to a tachycardia threshold. If the DF is above the tachycardia threshold, then a tachycardia is detected. Alternatively, if the DF is below the tachycardia threshold, then a tachycardia is not detected.

Fractionation Analysis

Figure 3:
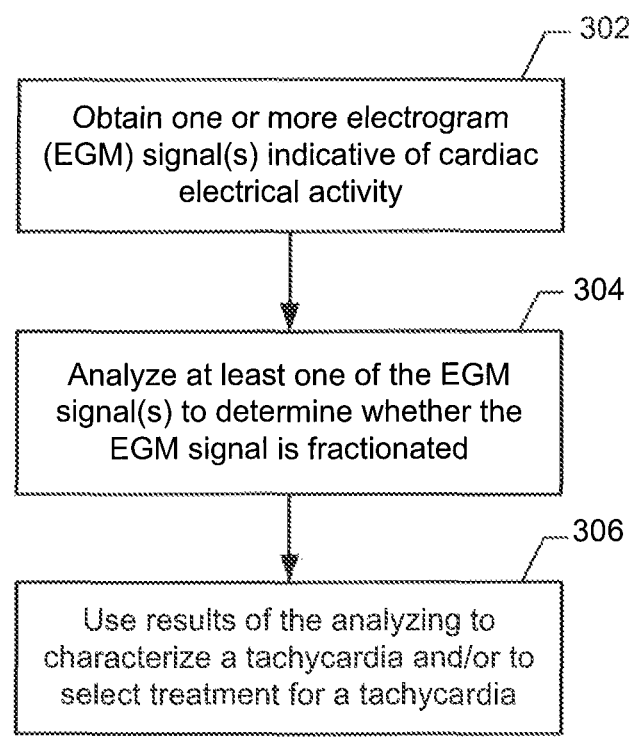
FIG. 3 is a high level flow diagram that is used to explain various embodiments of the present invention that can be used to characterize a tachycardia and/or to select treatment for a tachycardia using results of analyzing an electrogram for fractionation.

The high level flow diagram of FIG. 3 will now be used to explain various embodiments of the present invention that can be used to characterize a tachycardia and/or to select treatment for a tachycardia based upon a determination of whether an EGM signal is fractionated.

Referring to FIG. 3, at step 302, one or more EGM signal(s) indicative of cardiac electrical activity is/are obtained. At step 304, at least one of the EGM signal(s) obtained and step 302 is analyzed to determine whether the EGM signal is fractionated. In an embodiment, at least one EGM signal is analyzed only when a tachycardia is detected. In accordance with an embodiment, a fractionated EGM signal can be an EGM signal having two or more deflections crossing a specified threshold in a predetermined amount of time (e.g., a cardiac cycle). For example, in accordance with an embodiment, an EGM signal that is not fractionated will have only one deflection (e.g., an R-wave) crossing a threshold per cardiac cycle, while a fractionated EGM signal will have two or more deflections crossing the threshold per cardiac cycle. In accordance with an embodiment, the threshold can be at a baseline level (e.g., an isoelectrical signal level) or at some other level (e.g., between a noise floor and an R-wave threshold). Additionally, or alternatively, when viewed in the frequency domain, a fractionated EGM signal would have a power distribution over a broad range of frequencies, where a non-fractionated EGM signal would have power focused at only a few frequencies. In accordance with an embodiment, other techniques can be used to determine whether an EGM signal is fractionated.

At step 306, the result of the analysis (e.g., a fractionated EGM signal, or an EGM signal not fractionated) is used to characterize a tachycardia and/or select treatment for a tachycardia. For example, in accordance with an embodiment, the results of the analysis signal are used to characterize a tachycardia as one that is likely terminable using ATP or one that likely needs a shock to be terminated. In accordance with an embodiment, selecting treatment can be determining between delivering ATP to attempt to terminate a tachycardia, and delivering a shock to attempt to terminate the tachycardia without first delivering ATP. For example, in accordance with an embodiment, where only one EGM signal is analyzed to determine whether the one EGM signal is fractionated, and the one EGM signal analyzed is determined to not be fractionated, then ATP will be delivered to attempt to terminate the tachycardia. Alternatively, where only one EGM signal is analyzed to determine whether the one EGM signal is fractionated, and the one EGM signal is determined to be fractionated, then a shock will be delivered to attempt to terminate the tachycardia, without first delivering ATP.

Embodiments will be described where a complexity metric is determined for a fractionated EGM signal to quantify an extent of fractionation (e.g., the complexity of fractionation) of the EGM signal. In accordance with an embodiment, based on the complexity metric, a determination is made whether to deliver ATP to attempt to terminate a tachycardia, or whether to deliver a shock to attempt to terminate the tachycardia without first delivering ATP. For example, it is believed that the less complex the fractionated EGM signal the more likely that ATP can be used to successfully terminate a tachycardia, and the more complex the fractionated EGM signal the more likely a shock will be needed to terminate a tachycardia. Accordingly, a complexity threshold is set such that a complexity metric below a complexity threshold triggers ATP to attempt to terminate the tachycardia while a complexity metric above the complexity threshold triggers a shock to attempt to terminate the tachycardia without first delivering ATP. Additionally, in accordance with an embodiment, where results of analyzing the one EGM signal include determining that the one EGM signal is not fractionated, then ATP is delivered to attempt to terminate the tachycardia.

In accordance with an embodiment, the complexity metric is based on a deflection metric indicative of a number of deflections in the fractionated EGM signal, an amplitude metric indicative of an amplitude of one or more deflections in the fractionated EGM signal and/or an interval metric indicative of an interval of time between two or more deflections in the fractionated EGM signal. In an embodiment, the complexity metric can be a weighted sum of the deflection metric, the amplitude metric and the interval metric, where each metric can have a different weight associated therewith.

In accordance with an embodiment, the deflection metric is determined by determining a number of crossings of a threshold in a predetermined amount of time (e.g., in a cardiac cycle). In accordance with an embodiment, the amplitude metric is the average amplitude of the one or more deflections in a predetermined amount of time, the peak amplitude of the one or more deflections, or the minimum amplitude of the one or more deflections. Alternatively, the amplitude metric is the variation of amplitudes of the one or more deflections, and is determined by calculating the standard deviation, interquartile range, range, mean difference, median absolute deviation, average absolute deviation (or simply average deviation), coefficient of variation, quartile coefficient of dispersion, relative mean difference, variance (the square of the standard deviation) or variance-to-mean ratio, of the one or more deflections for a predetermined amount of time. The interval metric is the average interval of time, the largest interval of time, or the smallest interval of time between the two or more deflections. Use of alternative techniques for determining the deflection metric are within the scope of the present invention. Use of alternative techniques for determining the amplitude metric are within the scope of the present invention. Use of alternative techniques for determining the interval of time metric are within the scope of the present invention.

In accordance with an embodiment, the complexity threshold is defined based on a database of compiled fractionated EGM signals obtained from a broad patient population, along with information specifying a treatment (e.g., ATP or shock) that was successful or unsuccessful in terminating a tachycardia. For example, where ATP has generally been successful in terminating tachycardias characterized by a fractionated EGM signal having a first range of a complexity metric, but has generally been unsuccessful in terminating tachycardia characterized by a second range of the complexity metric, a complexity threshold is set such that a complexity metric less than a complexity threshold triggers the delivery of ATP to attempt to terminate the tachycardia, while a complexity metric that reaches a complexity threshold triggers a shock to attempt to terminate the tachycardia without first delivering ATP. It also within the scope of the present invention that the complexity threshold can be tailored to a specific patient, i.e., not just set based on a broad patient population.

FIG. 3 has been generally described as using a single EGM signal. However, embodiments described herein are useful where a plurality of EGM signals are obtained and included in an analysis. For example, in accordance with an embodiment, a plurality of EGM signals (e.g., at least two EGM signals) are obtained at step 302, where each of the EGM signals is obtained using a different sensing vector and thereby is indicative of cardiac electrical activity associated with a different cardiac region. In accordance with an embodiment, at step 304 at least two of the EGM signals are analyzed to determine whether the EGM signals are fractionated, and the results of the analysis are used to characterize a tachycardia and/or to select a treatment for a tachycardia at step 306.

In accordance with an embodiment, results of analyzing the plurality of EGM signals are used to determine whether to deliver ATP to attempt to terminate a tachycardia, or whether to deliver a shock to attempt to terminate the tachycardia without first delivering ATP. For example, in accordance with an embodiment, where a plurality of EGM signals are analyzed to determine whether each of the analyzed EGM signals is fractionated, and at least one of the EGM signals analyzed is determined to not be fractionated, then ATP is delivered using the pacing vector that is closest to the sensing vector used to obtain the EGM signal that is not fractionated. Alternatively, where results of analyzing the plurality of EGM signals include determining that all of the EGM signals analyzed are fractionated, then a shock will be delivered to attempt to terminate the tachycardia, without first delivering ATP.

In accordance with an embodiment, where each EGM signal analyzed is determined to be fractionated, a complexity metric indicative of a complexity of the fractionated EGM signal is determined, and based on the complexity metric determined for each fractionated EGM signal, a pacing vector is selected to use for delivering ATP. For example, in accordance with an embodiment, the complexity metric for at least two fractionated EGM signals is compared to one another in order to determine where ATP is to be delivered.

In one embodiment, ATP is delivered using a pacing vector that is closest to the sensing vector used to obtain the fractionated EGM signal having the lowest complexity metric, since the cardiac tissue paced by such a pacing vector is believed to be the most likely to be capable of being captured during an excitable gap, thereby enabling the pacing to take control of and terminate the tachycardia. Depending on implementation, a pacing vector that is closest to a sensing vector may or may not comprise the exact same electrodes as the sensing vector.

In an alternative embodiment, ATP is delivered using a pacing vector that is closest to the sensing vector used to obtain the EGM signal having the highest complexity metric, since the cardiac tissue paced by such a pacing vector is believed to be potentially closest to the source (i.e., the driver) of the tachycardia, and thereby may be susceptible to being overdriven by the pacing, and thus enabling the pacing to take control of and terminate the tachycardia. In accordance with an embodiment, in those cases where ATP is delivered but does not terminate the tachycardia within a predetermined amount of time, a shock can thereafter be delivered to attempt to terminate the tachycardia.

A fractionation analysis may be computationally (and thus, power and time) intensive. Thus, in certain embodiments the fractionation analysis is only performed after a tachycardia is detected using a less computationally intensive technique, such as, but not limited to, a technique that detects a tachycardia by comparing detected R-R intervals or heart rate to a corresponding threshold, which is well known in the art. In accordance with certain embodiments, if a tachycardia is detected that includes R-R intervals below a corresponding ventricular fibrillation (VF) interval threshold (or a heart rate above a corresponding VF rate threshold), then fractionation analysis can be skipped and a shock can be immediately delivered to attempt to terminate the VF as quickly as possible. In other embodiments, VF can initially be treated using ATP if the results of the fractionation analysis indicate that there is a good likelihood that ATP can be used to terminate the VF.

In accordance with other embodiments, results of a fractionation analysis are used to detect a tachycardia. For example, a fractionation complexity metric, examples of which were described above, is used to detect a tachycardia. In accordance with an embodiment, a determination of whether a tachycardia is detected is based on a comparison of the complexity metric to a tachycardia threshold. If the complexity metric is above the tachycardia threshold, then a tachycardia is detected. Alternatively, if the complexity metric is below the tachycardia threshold, then a tachycardia is not detected.

Exemplary Implantable System

Figure 4:
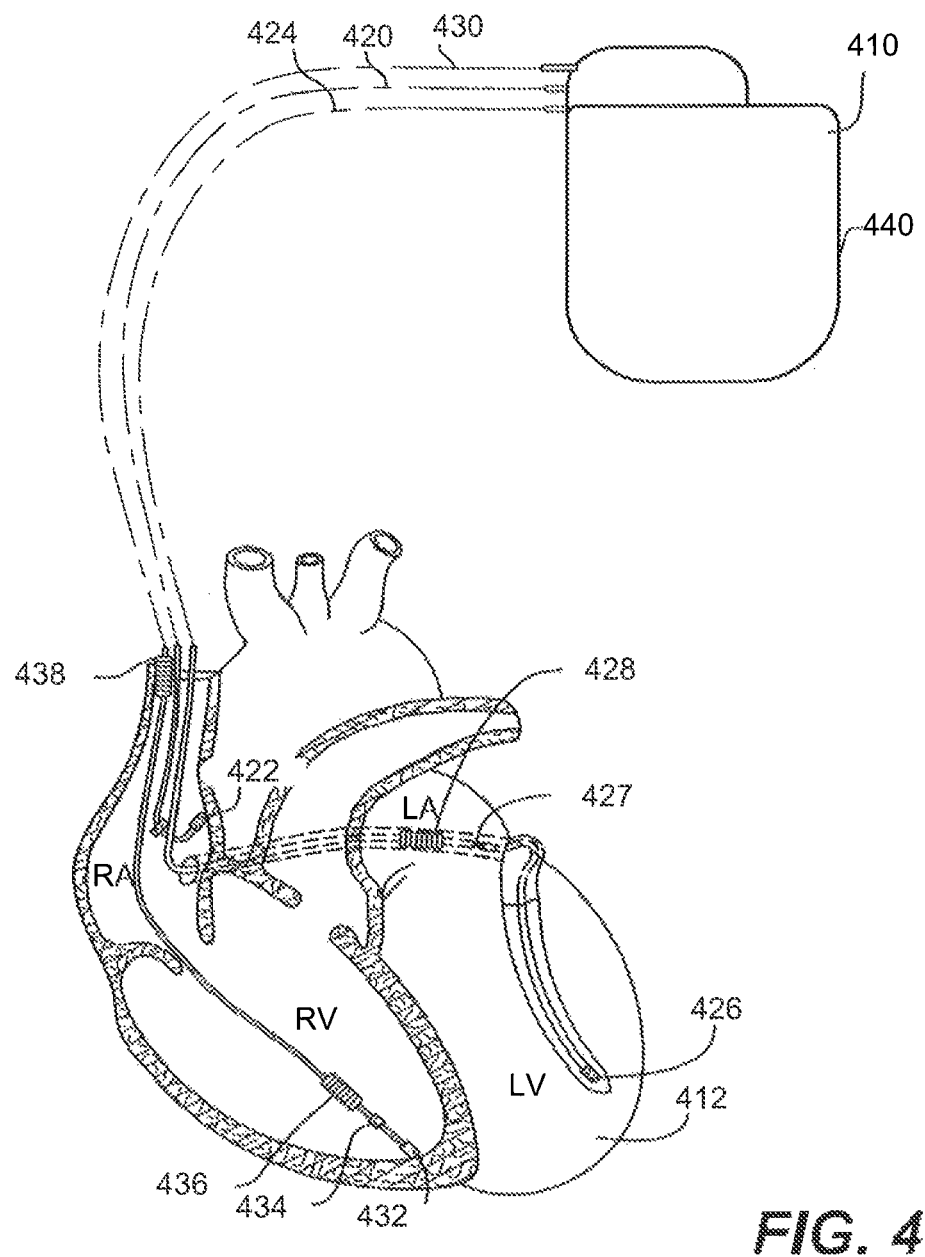
FIG. 4 illustrates an exemplary implantable cardiac stimulation device that can be used to perform various embodiments of the present invention.
Figure 5:
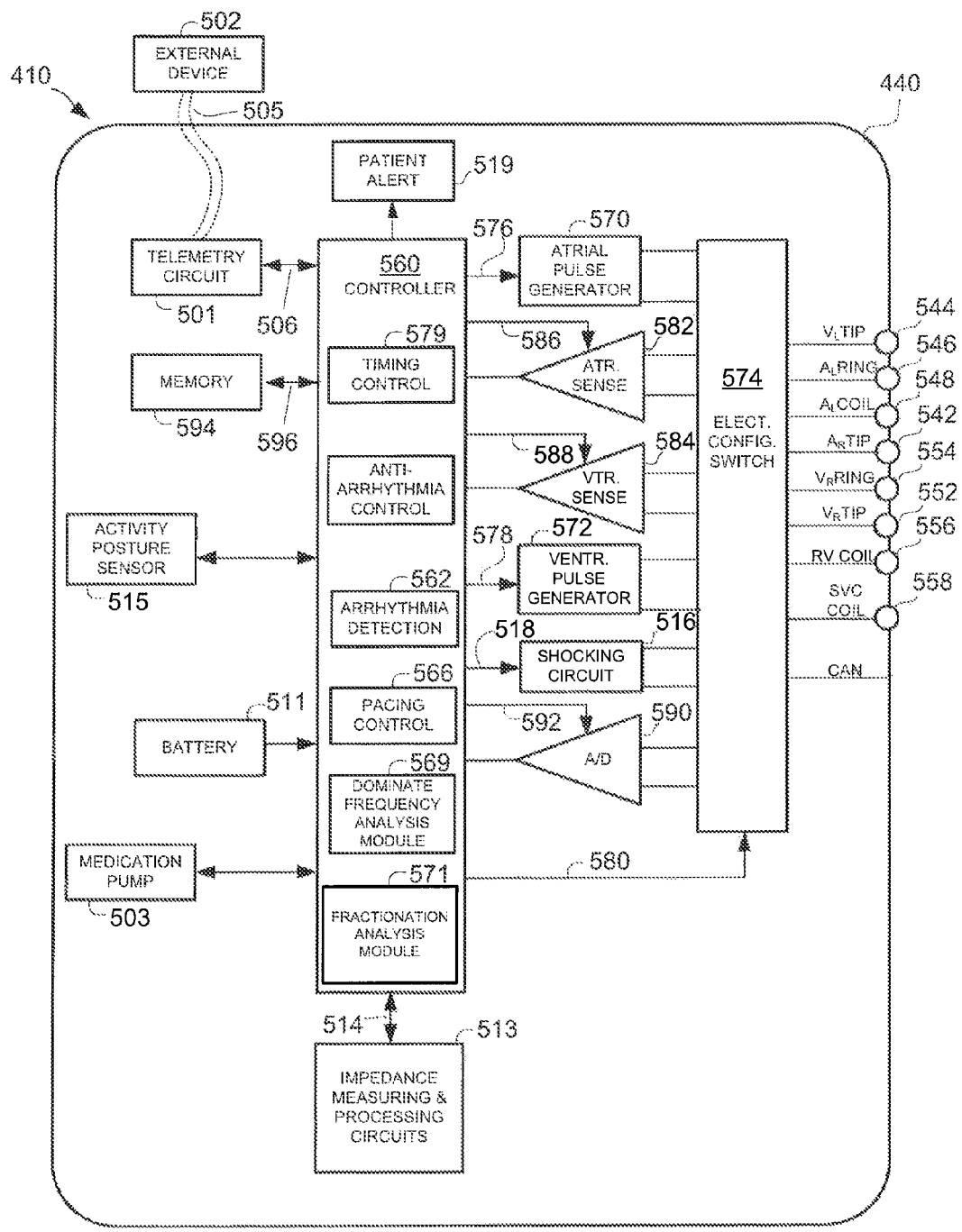
FIG. 5 is a simplified block diagram that illustrates possible components of the implantable device shown in FIG. 4.

FIGS. 4 and 5 will now be used to describe an exemplary implantable system that can be used to implement embodiments of the present invention including but not limited to characterizing a tachycardia and/or selecting treatment for a tachycardia using results of a dominant frequency analysis and a fractionation analysis. Referring to FIG. 4, the implantable system is shown as including an implantable stimulation device 410, which can be a pacing device and/or an implantable cardioverter defibrillator. The device 410 is shown as being in electrical communication with a patient's heart 412 by way of three leads, 420, 424 and 430, which can be suitable for delivering multi-chamber stimulation and shock therapy. The leads can also be used to obtain a thoracic impedance signal signals, for use in embodiments of the present invention.

To sense atrial cardiac signals and to provide right atrial chamber stimulation therapy, the device 410 is coupled to an implantable right atrial lead 420 having at least an atrial tip electrode 422, which typically is implanted in the patient's right atrial appendage. To sense left atrial and ventricular cardiac signals and to provide left-chamber pacing therapy, the device 410 is coupled to a "coronary sinus" lead 424 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428.

The device 410 is also shown in electrical communication with the patient's heart 412 by way of an implantable right ventricular lead 430 having, in this embodiment, a right ventricular tip electrode 432, a right ventricular ring electrode 434, a right ventricular (RV) coil electrode 436, and an SVC coil electrode 438. Typically, the right ventricular lead 430 is transvenously inserted into the heart 412 so as to place the right ventricular tip electrode 432 in the right ventricular apex so that the RV coil electrode 436 will be positioned in the right ventricle and the SVC coil electrode 438 will be positioned in the superior vena cava. Accordingly, the right ventricular lead 430 is capable of receiving cardiac signals and delivering stimulation in the form of pacing and shock therapy to the right ventricle.

FIG. 5 will now be used to provide some exemplary details of the components of the implantable devices 410. Referring now to FIG. 5, the implantable devices 410, and alternative versions thereof, can include a microcontroller 560. As is well known in the art, the microcontroller 560 typically includes a microprocessor, or equivalent control circuitry, and can further include RAM and/or ROM memory, logic and timing circuitry, state machine circuitry and/or I/O circuitry. Typically, the microcontroller 560 includes the ability to process or monitor input signals (data) as controlled by a program code stored in a designated block of memory. The details of the design of the microcontroller 560 are not critical to the present invention. Rather, any suitable microcontroller 560 can be used to carry out the functions described herein. The use of microprocessor-based control circuits for performing timing and data analysis functions are well known in the art. In specific embodiments of the present invention, the microcontroller 560 performs some or all of the steps associated with performing a DF analysis and/or a fractionation analysis of one or more EGM signals to characterize a tachycardia and/or to select treatment for a tachycardia. Additionally, the microcontroller 560 may detect arrhythmias, and select and control delivery of anti-arrhythmia therapy.

Representative types of control circuitry that may be used with embodiments of the present invention include the microprocessor-based control system of U.S. Pat. No. 4,940,052 (Mann et, al.) and the state-machines of U.S. Pat. No. 4,712, 555 (Sholder) and U.S. Pat. No. 4,944,298 (Sholder). For a more detailed description of the various timing intervals used within the pacing device and their inter-relationship, see U.S. Pat. No. 4,788,980 (Mann et, al.). The '052, '555, '298 and '980 patents are incorporated herein by reference.

Depending on implementation, the device 410 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, if the implantable device is a monitor that does not provide any therapy, it is clear that many of the blocks shown may be eliminated.

The housing 440, shown schematically in FIG. 5, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 can further include a connector (not shown) having a plurality of terminals, 542, 544, 546, 548, 552, 554, 556, and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522.

To achieve left atrial and ventricular sensing, pacing and shocking, the connector includes at least a left ventricular tip terminal ($V_L$ TIP) 544, a left atrial ring terminal ($A_L$ RING) 546, and a left atrial shocking terminal ($A_L$ COIL) 548, which are adapted for connection to the left ventricular tip electrode 526, the left atrial ring electrode 527, and the left atrial coil electrode 528, respectively.

To support right ventricle sensing, pacing and shocking, the connector further includes a right ventricular tip terminal ($V_R$ TIP) 552, a right ventricular ring terminal ($V_R$ RING) 554, a right ventricular shocking terminal ($R_V$COIL) 556, and an SVC shocking terminal (SVC COIL) 558, which are adapted for connection to the right ventricular tip electrode 432, right ventricular ring electrode 434, the RV coil electrode 436, and the SVC coil electrode 438, respectively.

An atrial pulse generator 570 and a ventricular pulse generator 572 generate pacing stimulation pulses for delivery by the right atrial lead 420, the right ventricular lead 430, and/or the coronary sinus lead 424 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators, or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry 579 which is used to control pacing parameters (e.g., the timing of stimulation pulses) as well as to keep track of the timing of refractory periods, noise detection windows, evoked response windows, alert intervals, marker channel timing, duration metrics, etc., which is well known in the art. Examples of pacing parameters include, but are not limited to, atrioventricular delay, interventricular delay and interatrial delay.

The switch bank 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, etc.) by selectively closing the appropriate combination of switches (not shown) as is known in the art.

Atrial sensing circuits 582 and ventricular sensing circuits 584 may also be selectively coupled to the right atrial lead 420, coronary sinus lead 424, and the right ventricular lead 430, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers, or shared amplifiers. The switch 574 determines the "sensing polarity" of the cardiac signal by selectively closing the appropriate switches, as is also known in the art. In this way, the clinician may program the sensing polarity independent of the stimulation polarity.

Each sensing circuit, 582 and 584, preferably employs one or more low power, precision amplifiers with programmable gain and/or automatic gain control, band-pass filtering, and a threshold detection circuit, as known in the art, to selectively sense the cardiac signal of interest. The automatic gain control enables the device 410 to deal effectively with the difficult problem of sensing the low amplitude signal characteristics of atrial or ventricular fibrillation. Such sensing circuits, 582 and 584, can be used to determine cardiac performance values used in the present invention. Alternatively, an automatic sensitivity control circuit may be used to effectively deal with signals of varying amplitude.

The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity, in the appropriate chambers of the heart. The sensing circuits, 582 and 584, in turn, receive control signals over signal lines, 586 and 588, from the microcontroller 560 for purposes of measuring cardiac performance at appropriate times, and for controlling the gain, threshold, polarization charge removal circuitry (not shown), and timing of any blocking circuitry (not shown) coupled to the inputs of the sensing circuits, 582 and 586.

As further shown in FIG. 5, the device 410 is also shown as having an impedance measuring and processing circuit 513 which is enabled by the microcontroller 560 via a control signal 514 and can be used for obtaining many types of bodily, intracardiac impedances, and thoracic impedances, including a network of single or multi-vector impedance measurements. Such impedance measurements can be used, e.g., for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 513 may be coupled to the switch 574 so that any desired electrodes may be used, and networks of vectors can be selected.

In accordance with an embodiment, the implantable device 410 includes a dominant frequency (DF) analysis module 569. The DF analysis module 569 can be used to perform DF analysis of one or more EGM signals to characterize a tachycardia and/or to select treatment for a tachycardia using the techniques described above with reference to FIG. 1 and FIGS. 2A-2C. In certain embodiments, the DF analysis module is configured to determine whether ATP will be delivered to attempt to terminate the tachycardia, or whether a shock will be delivered to attempt to terminate the tachycardia without first delivering ATP.

In accordance with an embodiment, the implantable device 410 further includes a fractionation analysis module 571. The fractionation analysis module 571 can be used to analyze one or more EGM signals to determine whether the EGM signal (s) is/are fractionated, and to characterize a tachycardia and/or to select treatment for a tachycardia based on results of the analysis using the techniques described above with reference to FIG. 3. In certain embodiments, the fractionation analysis module 571 uses results of the analysis to determine whether to deliver anti-tachycardia pacing (ATP) to attempt to terminate a tachycardia, or whether to deliver a shock to attempt to terminate the tachycardia without first delivering ATP.

The DF analysis module 569 and the fractionation analysis module 571 can be implemented within the microcontroller 560, as shown in FIG. 5, and can be implemented by software, firmware, or combinations thereof. It is also possible that all or portions of the DF analysis module 569 and the fractionation analysis module 571 can be implemented separate from the microcontroller 560.

The implantable device can also include a medication pump 503, which can deliver medication to a patient if the detected dominant frequencies fall outside certain thresholds or ranges. Information regarding implantable medication pumps may be found in U.S. Pat. No. 4,731,051 (Fischell) and in U.S. Pat. No. 4,947,845 (Davis), both of which are incorporated by reference herein.

For arrhythmia detection, the device 410 includes an arrhythmia detector 562 that utilizes the atrial and ventricular sensing circuits, 582 and 584, to sense cardiac signals to determine whether a rhythm is physiologic or pathologic. The timing intervals between sensed events (e.g., P-waves, R-waves, and depolarization signals associated with fibrillation) can be classified by the microcontroller 560 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 562 can perform arrhythmia discrimination, e.g., using measures of arterial blood pressure determined in accordance with embodiments of the present invention. The arrhythmia detector 562 can be implemented within the microcontroller 560, as shown in FIG. 5. Thus, this detector 562 can be implemented by software, firmware, or combinations thereof. It is also possible that all, or portions, of the arrhythmia detector 562 can be implemented using hardware. Further, it is also possible that all, or portions, of the ischemia detector 562 can be implemented separate from the microcontroller 560.

The implantable device 410 can also include a pacing controller 566, which can adjust a pacing rate and/or pacing intervals based on detected dominant frequencies, in accordance with embodiments of the present invention. The pacing controller 566 can be implemented within the microcontroller 560, as shown in FIG. 5. Thus, the pacing controller 566 can be implemented by software, firmware, or combinations thereof. It is also possible that all, or portions, of the pacing controller 566 can be implemented using hardware. Further, it is also possible that all, or portions, of the pacing controller 566 can be implemented separate from the microcontroller 560.

Still referring to FIG. 5, cardiac signals are also applied to the inputs of an analog-to-digital (A/D) data acquisition system 590. The data acquisition system 590 can be configured to acquire various signals, including but not limited to, CI, IEGM, PPG and IPG signals, convert the raw analog data into a digital signal, and store the digital signals for later processing and/or telemetric transmission to an external device 502. The data acquisition system 590 can be coupled to the right atrial lead 420, the coronary sinus lead 424, and the right ventricular lead 430 through the switch 574 to sample cardiac signals across any pair of desired electrodes.

The data acquisition system 590 can be coupled to the microcontroller 560, or other detection circuitry, for detecting an evoked response from the heart 412 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 560 detects a depolarization signal during a window following a stimulation pulse, the presence of which indicates that capture has occurred. The microcontroller 560 enables capture detection by triggering the ventricular pulse generator 572 to generate a stimulation pulse, starting a capture detection window using the timing control circuitry 579 within the microcontroller 560, and enabling the data acquisition system 590 via control signal 592 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 560 is further coupled to the memory 594 by a suitable data/address bus 596, wherein the programmable operating parameters used by the microcontroller 560 are stored and modified, as required, in order to customize the operation of the implantable device 410 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 412 within each respective tier of therapy. The memory 594 can also store data including information about detected dominant frequencies, the selected treatment for the detected dominant frequency, and how subsequent dominant frequencies change, if at all, as a result of the selected treatment.

The operating parameters of the implantable device 410 may be non-invasively programmed into the memory 694 through a telemetry circuit 501 in telemetric communication with an external device 502, such as a programmer, transtelephonic transceiver, or a diagnostic system analyzer. The telemetry circuit 501 can be activated by the microcontroller 560 by a control signal 506. The telemetry circuit 501 advantageously allows intracardiac electrograms and status information relating to the operation of the device 410 (as contained in the microcontroller 560 or memory 594) to be sent to the external device 502 through an established communication link 505. The telemetry circuit can also be use to transmit arterial blood pressure data to the external device 502.

For examples of telemetry devices, see U.S. Pat. No. 4,809,697, entitled "Interactive Programming and Diagnostic System for use with Implantable Pacemaker" (Causey, III et al.);

U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 410 additionally includes a battery 511 which provides operating power to all of the circuits shown in FIG. 5. If the implantable device 410 also employs shocking therapy, the battery 511 should be capable of operating at low current drains for long periods of time, and then be capable of providing high-current pulses (for capacitor charging) when the patient requires a shock pulse. The battery 511 should also have a predictable discharge characteristic so that elective replacement time can be detected.

The implantable device 410 is also shown as including an activity and/or posture sensor 515. Such a sensor 515 can be a simple one dimensional sensor that converts mechanical motion into a detectable electrical signal, such as a back electro magnetic field (BEMF) current or voltage, without requiring any external excitation. Alternatively, the sensor 515 can measure multi-dimensional activity information, such as two or more of acceleration, direction, posture and/or tilt. Examples of multi-dimensional activity sensors include, but are not limited to: the three dimensional accelerometer-based position sensor disclosed in U.S. Pat. No. 6,658,292 to Kroll et al., which is incorporated herein by reference; the AC/DC multi-axis accelerometer disclosed in U.S. Pat. No. 6,466,821 to Pianca et al., which in incorporated herein by reference; and the commercially available precision dual-axis accelerometer model ADXL203 and three-axis accelerometer model ADXL346, both available from Analog Devices of Norwood, Mass.

The implantable device 410 can also include a magnet detection circuitry (not shown), coupled to the microcontroller 560. It is the purpose of the magnet detection circuitry to detect when a magnet is placed over the implantable device 410, which magnet may be used by a clinician to perform various test functions of the implantable device 410 and/or to signal the microcontroller 560 that the external programmer 502 is in place to receive or transmit data to the microcontroller 560 through the telemetry circuits 501.

In the case where the implantable device 410 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 560 further controls a shocking circuit 516 by way of a control signal 518. The shocking circuit 516 generates shocking pulses of low (up to 0.5 Joules), moderate (0.5-10 Joules), or high energy (11 to 40 Joules), as controlled by the microcontroller 560. Such shocking pulses are applied to the patient's heart 412 through at least two shocking electrodes, and as shown in this embodiment, selected from the left atrial coil electrode 428, the RV coil electrode 436, and/or the SVC coil electrode 438. As noted above, the housing 440 may act as an active electrode in combination with the RV coil 436, or as part of a split electrical vector using the SVC coil electrode 438 or the left atrial coil electrode 428 (i.e., using the RV electrode as a common electrode).

The above described implantable device 410 was described as an exemplary pacing device. One or ordinary skill in the art would understand that embodiments of the present invention can be used with alternative types of implantable devices. Accordingly, embodiments of the present invention should not be limited to use only with the above described device.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 1-3. Further, it is possible to change the order of some of the steps shown in FIGS. 1-3, without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for use with an implantable system, comprising:
    (a) obtaining one or more electrogram (EGM) signal(s) indicative of cardiac electrical activity;
    (b) analyzing at least one of the EGM signal(s) to determine whether the EGM signal is fractionated, wherein step (b) comprises:
        (b.1) analyzing only one EGM signal to determine whether the one EGM signal is fractionated; and
        (b.2) if the one EGM signal is determined to be fractionated, then also determining a complexity metric indicative of a complexity of the fractionated EGM signal; and
    (c) using results of the analyzing to characterize a tachycardia and/or to select treatment for a tachycardia, wherein step (c) comprises:
        (c.1) if the one EGM signal is determined to not be fractionated, then determining that ATP will be delivered to attempt to terminate the tachycardia;
        (c.2) if the one EGM signal is determined to be fractionated and the complexity metric does not exceed a complexity threshold, then determining that ATP will be delivered to attempt to terminate the tachycardia; and
        (c.3) if the one EGM signal is determined to be fractionated and the complexity metric exceeds the complexity threshold, then determining that a shock will be delivered to attempt to terminate the tachycardia, without first delivering ATP.

2. The method of claim 1, wherein steps (b) and (c) are performed in response to a tachycardia being detected.

3. The method of claim 1, wherein:
    step (b.2) comprises
    (b.2.1) determining a deflection metric indicative of a number of deflections in the fractionated EGM;
        (b.2.2) determining an amplitude metric indicative of an amplitude of one or more deflections in the fractionated EGM; and/or
        (b.2.3) determining an interval metric indicative of an interval of time between two or more deflections in the fractionated EGM; and
        (b.2.4) determining, based on the deflection metric, the amplitude metric and/or the interval metric, a complexity metric indicative of a complexity of the fractionated EGM signal.

4. A method for use with an implantable system, comprising:
(a) obtaining one or more electrogram (EGM) signal(s) indicative of cardiac electrical activity;
(b) analyzing at least one of the EGM signal(s) to determine whether the EGM signal is fractionated; and
(c) using results of the analyzing to characterize a tachycardia and/or to select treatment for a tachycardia, wherein:
step (b) comprises analyzing a plurality of EGM signals to determine whether each of the analyzed EGM signals is fractionated; and
step (c) includes using results of the analyzing the plurality of EGM signals to characterize a tachycardia and/or to select a treatment for a tachycardia.

5. The method of claim 4, wherein step (c) includes using results of the analyzing the plurality of EGM signals to determine whether to deliver anti-tachycardia pacing (ATP) to attempt to terminate a tachycardia, or whether to deliver a shock to attempt to terminate the tachycardia without first delivering ATP.

6. The method of claim 5, wherein step (c) comprises:
(c.1) if at least one the EGM signals analyzed at step (b) is determined to not be fractionated, then determining that ATP will be delivered to attempt to terminate the tachycardia; and
(c.2) if all of the EGM signals analyzed at step (b) are determined to be fractionated, then determining that a shock will be delivered to attempt to terminate the tachycardia, without first delivering ATP.

7. The method of claim 6, wherein step (c.1) includes using results of the analyzing the plurality of EGM signals to select a pacing vector to use for delivering ATP.

8. The method claim 4, wherein:
step (b) further comprises determining for each EGM signal determined to be fractionated, a complexity metric indicative of a complexity of the fractionated EGM signal; and
step (c) further comprises selecting a pacing vector to use for delivering ATP based on the complexity metric determined for each EGM signal determined to be fractionated.

9. An implantable system, comprising:
one or more pulse generator configured to deliver pacing therapy;
one or more sensing circuit configured to obtain one or more electrogram (EGM) signal(s) indicative of cardiac electrical activity;
one or more shocking circuit configured to deliver a shock;
a fractionation analysis module configured to
analyze at least one of the EGM signal(s) to determine whether the EGM signal is fractionated; and
characterize a tachycardia and/or to select treatment for a tachycardia based on results of the analysis, wherein the fractionation analysis module is also configured to:
analyze only one EGM signal to determine whether the one EGM signal is fractionated, and if the one EGM signal is determined to be fractionated, then also determine a complexity metric indicative of a complexity of the fractionated EGM signal, wherein
if the one EGM signal is determined to not be fractionated, then determine that ATP will be delivered to attempt to terminate the tachycardia; and
if the one EGM signal is determined to be fractionated and the complexity metric does not exceed a complexity threshold, then determine that ATP will be delivered to attempt to terminate the tachycardia; and
if the one EGM signal is determined to be fractionated and the complexity metric exceeds a complexity threshold, then determine that a shock will be delivered to attempt to terminate the tachycardia, without first delivering ATP.

10. The implantable system of claim 9, wherein the fractionation analysis module is configured to:
determine a deflection metric indicative of a number of deflections in the fractionated EGM;
determine an amplitude metric indicative of an amplitude of one or more deflections in the fractionated EGM; and/or
determine an interval metric indicative of an interval of time between two or more deflections in the fractionated EGM; and
determine, based on the deflection metric, the amplitude metric and/or the interval metric, a complexity metric indicative of a complexity of the fractionated EGM signal.

11. An implantable system, comprising:
one or more pulse generator configured to deliver pacing therapy;
one or more sensing circuit configured to obtain one or more electrogram (EGM) signal(s) indicative of cardiac electrical activity;
one or more shocking circuit configured to deliver a shock;
a fractionation analysis module configured to:
analyze at least one of the EGM signal(s) to determine whether the EGM signal is fractionated; and
characterize a tachycardia and/or to select treatment for a tachycardia based on results of the analysis, wherein:
the one or more sensing circuit is/are configured to obtain a plurality of EGM signals, wherein each of the EGM signals is obtained using a different sensing vector and thereby is indicative of cardiac electrical activity associated with a different cardiac region; and
the fractionation analysis module is also configured to:
perform analysis of at least two of the EGM signals to determine whether the EGM signals comprise a fractioned electrogram;
use results of the analysis of the EGM signals to characterize a tachycardia and/or to select a treatment for a tachycardia
use results of the analysis of at least two of the EGM signals to determine whether to deliver anti-tachycardia pacing (ATP) to attempt to terminate a tachycardia, or whether to deliver a shock to attempt to terminate the tachycardia without first delivering ATP;
determine that ATP will be delivered to attempt to terminate the tachycardia if at least one of the EGM signals analyzed is determined to not be fractionated; and
determine that a shock will be delivered to attempt to terminate the tachycardia, without first delivering ATP if all of the EGM signals analyzed are determined to be fractionated.

12. An implantable system, comprising:
one or more pulse generator configured to deliver pacing therapy;
one or more sensing circuit configured to obtain one or more electrogram (EGM) signal(s) indicative of cardiac electrical activity;
one or more shocking circuit configured to deliver a shock;
a fractionation analysis module configured to
analyze at least one of the EGM signal(s) to determine whether the EGM signal is fractionated;

characterize a tachycardia and/or to select treatment for a tachycardia based on results of the analysis determine for each EGM signal determined to be fractionated, a complexity metric indicative of a complexity of the fractionated EGM signal; and select a pacing vector to use for delivering ATP based on the complexity metric determined for each EGM signal determined to be fractionated.

13. The implantable system of claim 12, wherein the fractionation analysis module is also configured to use results of the analysis to determine whether to deliver anti-tachycardia pacing (ATP) to attempt to terminate a tachycardia, or whether to deliver a shock to attempt to terminate the tachycardia without first delivering ATP.

* * * * *